United States Patent [19]

Nasser

[11] Patent Number: 5,437,181
[45] Date of Patent: Aug. 1, 1995

[54] CONCRETE SLUMP TESTING

[75] Inventor: Karim W. Nasser, Saskatoon, Canada

[73] Assignee: University of Saskatchewan, Saskatchewan, Canada

[21] Appl. No.: 199,957

[22] Filed: Feb. 22, 1994

[51] Int. Cl.$^6$ ............................................. G01N 11/02
[52] U.S. Cl. .................................. 73/54.03; 73/54.01
[58] Field of Search ............... 73/54.03, 54.01, 864.64, 73/864.44, 864.65, 78, 81

[56] References Cited

U.S. PATENT DOCUMENTS

| | | | |
|---|---|---|---|
| 2,422,634 | 6/1947 | Riepert et al. | 73/81 |
| 3,492,857 | 2/1970 | Bosco et al. | 73/54.01 |
| 3,863,494 | 2/1975 | Nasser | 73/54.03 |
| 4,332,158 | 6/1982 | Osborne | 73/54.03 |
| 4,530,235 | 7/1985 | Shabel | 73/81 |
| 4,801,865 | 1/1989 | Miller et al. | 324/65 R |
| 4,866,997 | 9/1989 | Kaufman | 73/864.63 |

FOREIGN PATENT DOCUMENTS

| | | | |
|---|---|---|---|
| 0204434 | 12/1982 | Japan | 73/54.01 |
| 0161436 | 7/1986 | Japan | 73/54.01 |
| 8001444 | 10/1981 | Netherlands | 73/54.01 |
| 2092308 | 8/1982 | United Kingdom | 73/54.03 |

OTHER PUBLICATIONS

K. W. Nasser, "New and Simple Tester for Slump of Concrete", ACI Journal, Oct. 1976, pp. 561–565.
K. W. Nasser, "A New Method for Evaluatiion of the Slump of Concrete", ACI Journal Special Publication, SP 144–27, Mar. 1994, pp. 575–587.

Primary Examiner—Richard E. Chilcot, Jr.
Assistant Examiner—James M. Olsen
Attorney, Agent, or Firm—Murray E. Thrift; Adrian D. Battison; Stanley G. Ade

[57] ABSTRACT

A slump tester for concrete includes a testing unit and a measuring unit. The testing unit includes a tube with a perforated lower section that is lowered into the concrete to be tested up to the level of a disc carried on the tube. A timer button on the measuring unit is pushed to initiate a timer. After a preset time, an alarm sounds and the rod-like measuring unit is lowered into the tube until contact is made with the concrete that has entered the testing unit. This is indicated by a dot appearing in a digital display on the upper end of the measuring unit. The depth to which the rod has been lowered into the tube is monitored using an induction coil wound on the upper part of the rod and a metal cylinder in the upper end of the testing unit. The inductance of the coil varies linearly with the degree of insertion and this is used to generate a signal representing the slump of the concrete, which is displayed on the measuring unit display. The measuring unit also includes a temperature sensor near the bottom end of the rod so that temperature can also be displayed on the measuring unit.

12 Claims, 4 Drawing Sheets

CONCRETE SLUMP TESTING

FIELD OF THE INVENTION

The present invention relates to concrete testing and more particularly to the measuring of slump in fresh concrete.

BACKGROUND

The applicant's U.S. Pat. No. 3,863,494, granted Feb. 4, 1975, the disclosure of which is incorporated herein by reference, describes a slump tester for measuring "K-slump". That tester consists of a testing unit and a measuring unit. The testing unit is an elongate tube with upper and lower sections separated by a disc floater surrounding and fixed to the tube. The lower section is apertured so that when it is immersed in fresh concrete, the concrete will flow into the tube at a rate representative of its slump. The measuring unit is a calibrated rod that extends into the tube to measure the height of the concrete that has entered after a predetermined time.

The present invention relates to certain improvements in such a tester.

SUMMARY

According to one aspect of the present invention there is provided a concrete slump tester comprising:
  a measuring unit comprising an elongate rod, an inductance coil mounted on the rod and means for measuring the inductance of the coil;
  a testing unit comprising a tube for receiving the rod therein, the tube having a lower section for insertion into a body of fresh concrete, an upper section, a plurality of openings in the lower section of the tube for allowing fresh concrete surrounding the lower section of the tube to enter the lower section of the tube at a rate depending on the slump of the concrete, and inductance modifying means mounted on the tube for modifying the inductance of the coil as a function of the depth of penetration of the rod into the tube.

The coil inductance is a function of the depth of penetration of the rod into the tube and represents the height of concrete in the tube when the rod is placed in contact with the concrete. A reading of the inductance is therefore a measure of the concrete slump. This may be displayed, for example on a digital read-out.

According to another aspect of the present invention there is provided a concrete slump tester comprising:
  a testing unit including a tube with a lower section, an upper section and at least one opening in the lower section to allowing fresh concrete to enter the tube;
  a measuring unit comprising an elongate rod sized to extend into the testing unit and having a bottom end for engaging concrete in the tube, electrode means on the bottom end of the rod and circuit means coupled to the electrode means and responsive to contact of the electrode means with fresh concrete for generating a contact signal, and means for measuring the depth of the rod in the tube.

The electrodes on the bottom end of the rod are electrically bridged when they contact the wet concrete. This closes the electric circuit containing the electrodes to generate a signal, clearly indicating when the rod has reached the upper limits of the concrete that has migrated into the tube.

It is preferred to include a temperature sensor in the end of the rod, so that the temperature of the concrete can be measured at the time of testing.

The measuring unit may also include a countdown timer for counting down the period over which the concrete is allowed to enter the testing unit before a measurement is taken.

The measuring unit preferably has an instrument head on its upper end, carrying a digital display and a set of switches for selecting time, temperature or slump display. The contact of the rod with the wet concrete is displayed with an independent light on the display.

An exemplary embodiment of the present invention will now be described by way of example.

BRIEF DESCRIPTION OF THE DRAWINGS

In the accompanying drawings, which illustrate an exemplary embodiment of the present invention.

DETAILED DESCRIPTION

Figure 2:
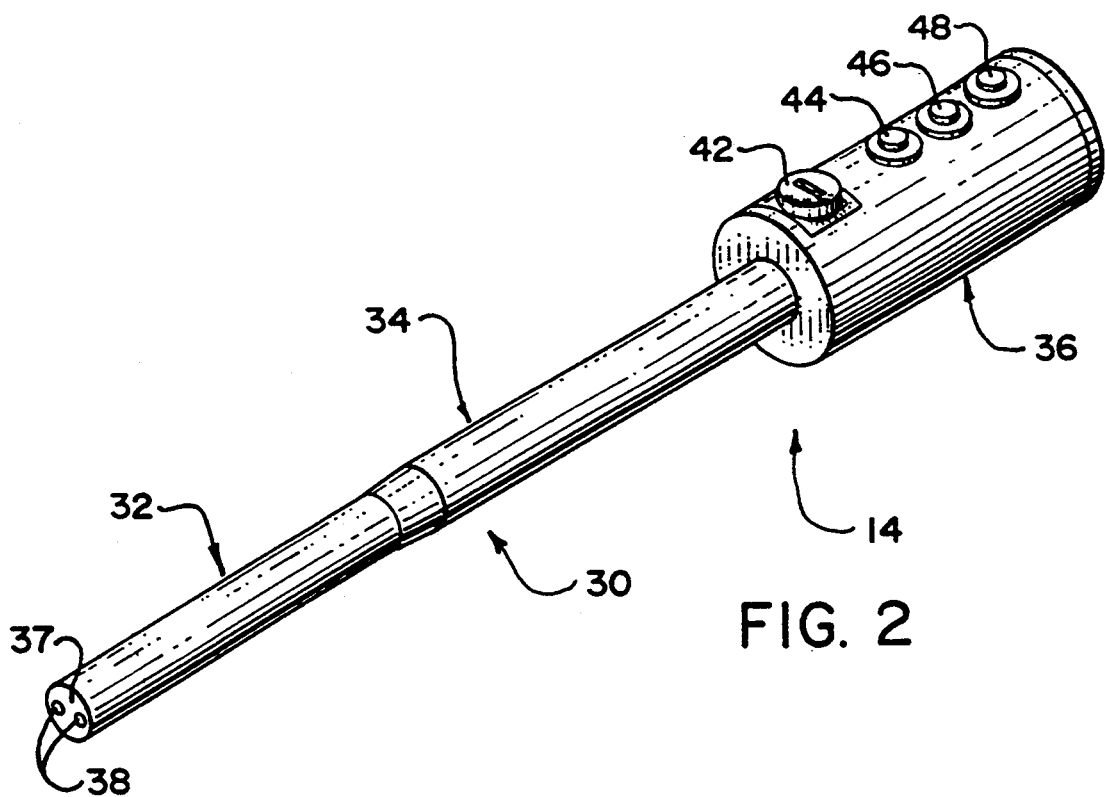
FIG. 2 is an isometric view of a measuring unit of a tester according to the present invention.
Figure 1:
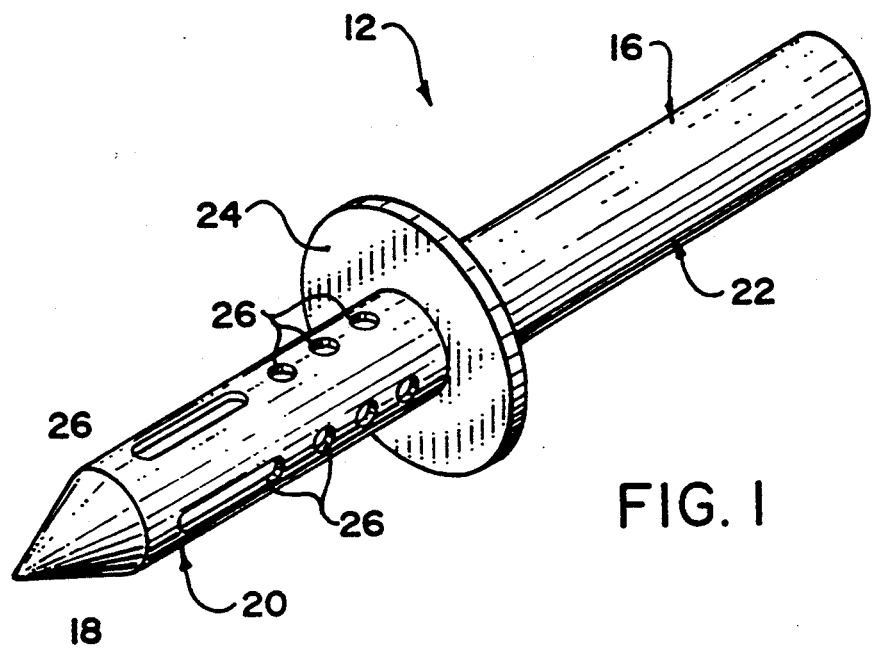
FIG. 1 is an isometric view of a testing unit of a tester according to the present invention.
Figure 3:
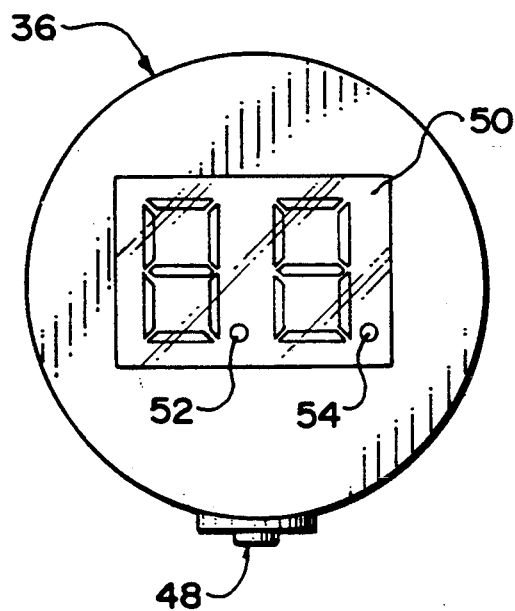
FIG. 3 is an end view of the measuring unit.

Referring to the accompanying drawings, there is illustrated a concrete slump tester 10. This consists of a testing unit 12 and a measuring unit 14. The testing unit includes a thermoplastic tube 16 with a conical tip 18 at the lower end. The tube is divided into a lower section 20 and an upper section 22 by an annular floater disc 24 secured to the outside of the tube. The lower section 20 has a series of apertures 26 formed in it to allow the entry of fresh concrete when the lower section of the tube is inserted into a body of fresh concrete.

Figure 4:
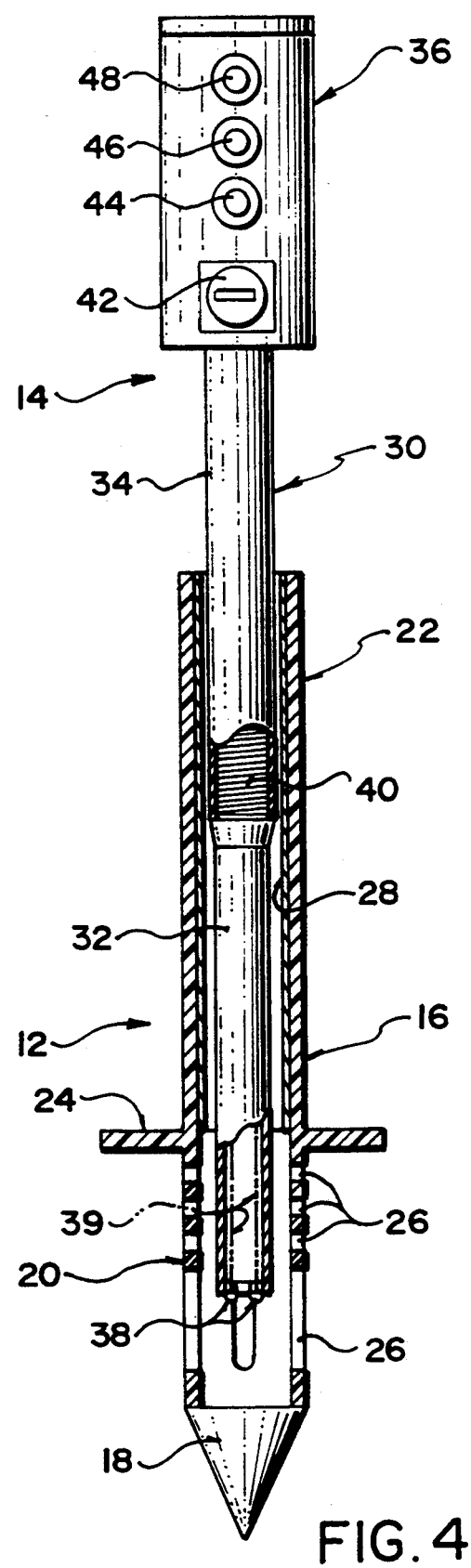
FIG. 4 is a side view of the tester, partly in cross section.

As illustrated most particularly in FIG. 4, the upper section 22 of the tube is lined with an aluminum foil cylinder 28.

The measuring unit 14 includes a measuring rod 30. This has a lower section 32 and an upper section 34. An enlarged instrument head 36 is mounted on the upper end of the upper section. At the bottom end 37 of the measuring rod are two electrodes 38 connected by respective wires 39 to the circuitry within the instrument head as will be described more fully in the following.

The upper section 34 of the rod is surrounded by an inductance coil 40 also connected to the electrical circuitry within the instrument head.

The instrument head contains a battery holder 42. Three switches, a slump switch 44, a timer switch 46 and a temperature switch 48 are mounted on the side of this cylindrical head. The top end of the head has a two-digit display 50 to display time, temperature or slump. The display has two decimal points, a point 52 which indicates contact of the bottom end of the rod 30 with wet concrete and a point 54 that represents a low battery signal.

Figure 5A:
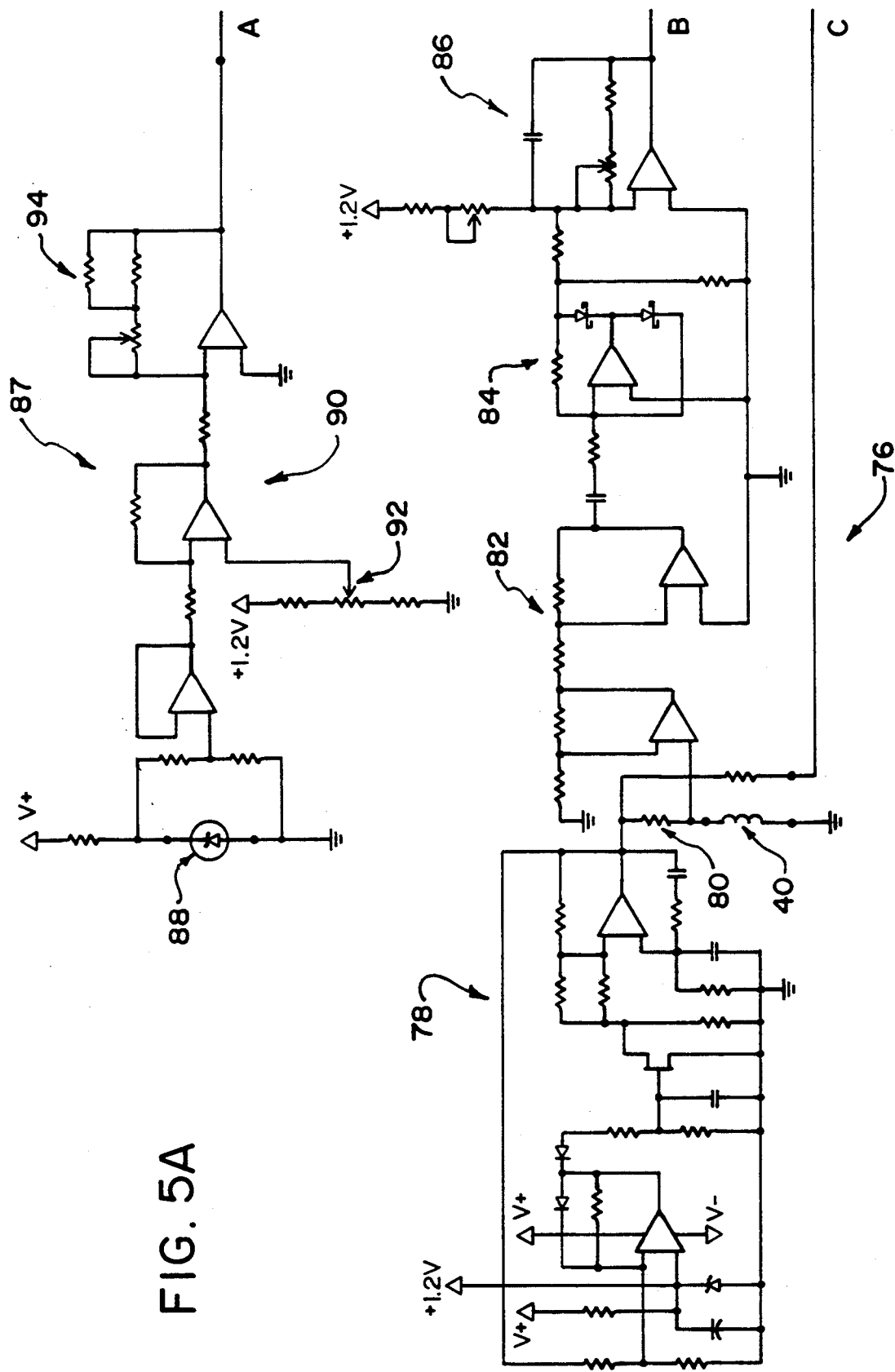
FIGS. 5A and 5B together present an electrical schematic of the tester.
Figure 5B:
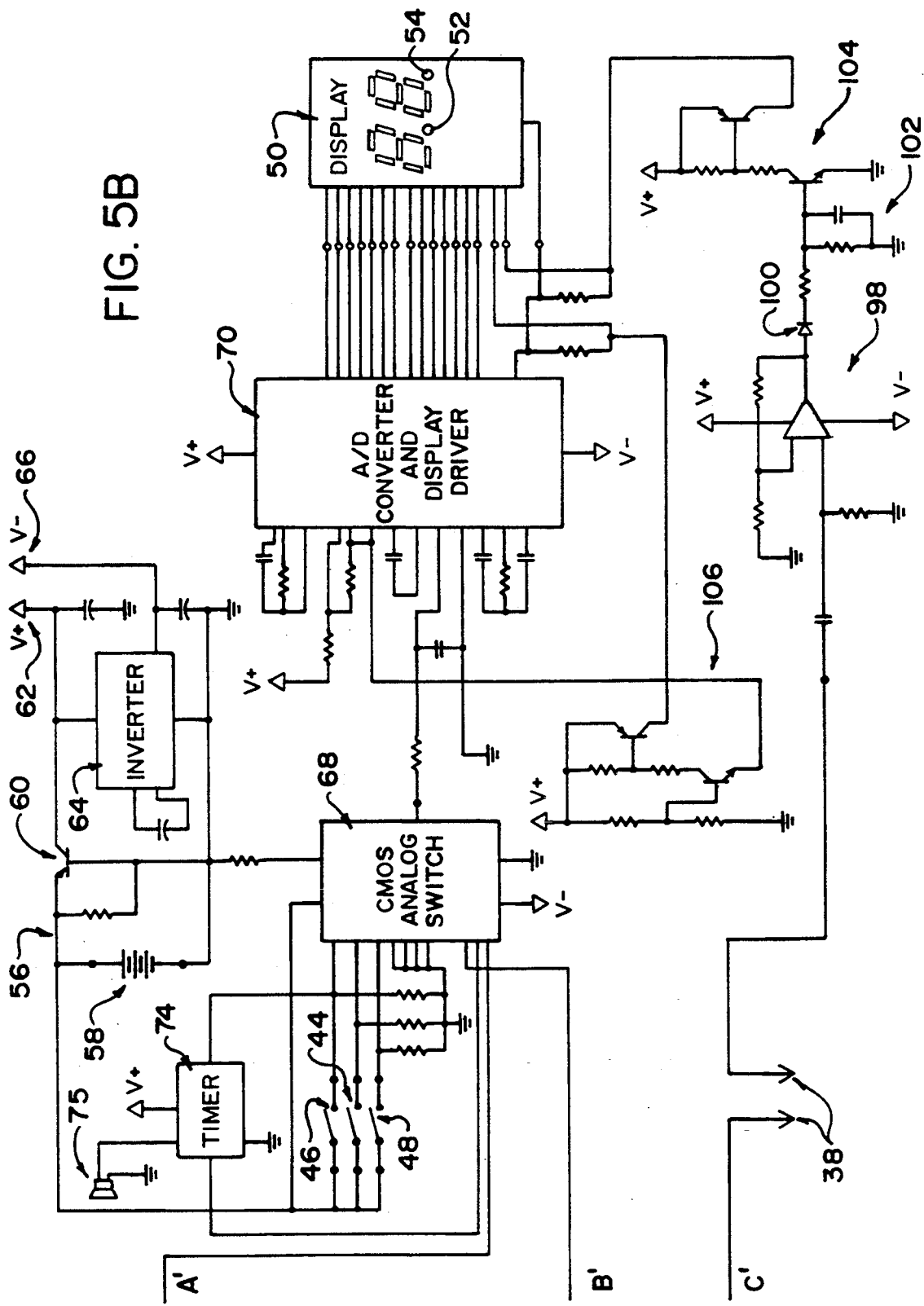

FIGS. 5A and 5B show the electrical schematic of the tester. Referring to those drawings, the tester includes a power supply circuit 56. This includes a battery 58 that supplies the power for the unit. A switching transistor 60, when actuated, connects the positive terminal of the battery to the positive output 62 of the power supply, providing positive supply voltage v+.

That positive output is also connected to the positive input of an inverter 64 which produces an "inverted" voltage v− at the negative output 66.

The switching transistor 60 is controlled by a CMOS analog switch 68. The transistor is turned on when any one of the slump, timer and temperature switches 44, 46 and 48 respectively is closed. These three switches connect battery power to the analog switch, which in turn turns on the transistor 60 to provide power to all of the circuits in the tester. The switch also has an output to an analog to digital converter and display driver 70 which in turn drives the display 50. When the timer switch 46 is closed, this activates a countdown timer 74 and causes the analog switch 68 to connect the timer output to the display driver 70. When the timer is counted out, a buzzer 75 sounds.

When the slump switch 44 is closed, the signal from a slump signal circuit 76 is connected by the analog switch to the display driver 70, The slump signal circuit 76 includes a Wien-Bridge oscillator 78 with a 40 KHz output. This output is connected through a resister 80 to the inductance coil 40 on the rod 30. The inductance of this coil changes linearly with its position in the aluminum tube 28, By feeding the coil with the current source 80, a voltage is produced that represents the position of the coil in the aluminum tube. This voltage is amplified in an amplifier 82, rectified in half-wave rectifier 84 and then passed to a filter and direct current amplifier 86 to provide a slump signal to the analog switch. The output at the digital display 50 is a flow number that correlates closely with the slump of the concrete.

When the temperature switch 48 is closed, it causes the analog switch 68 to connect a temperature signal from a temperature sensor circuit 87 to the display driver 70. The temperature sensor circuit 87 includes a temperature sensor 88 with an output to a three-stage temperature sensor amplifier 90. The second stage of this amplifier has a zero adjust circuit 92, while the third stage has a gain adjustment 94.

One of the electrodes 38 is supplied with an AC voltage signal from the Wien-Bridge oscillator 78. The second electrode 38 is connected to an AC amplifier 98. The output of this amplifier is rectified and filtered by diode 100 and RC filter 102 to operate a switching circuit 104 that passes positive supply voltage to the display to illuminate the decimal point 52 on the display 50 when the electrodes are bridged by wet concrete.

Another switching circuit 106 monitors the battery voltage and illuminates the second decimal point 54 on the display when the battery voltage drops below an acceptable level.

In operation of the tester, the testing unit is inserted into the concrete to be tested until the disc 24 rests on top of the concrete. The timer switch 46 is then pressed, causing the timer 74 to count down the time necessary for the concrete to enter the lower section of the testing unit tube. When the timer counts out, the buzzer sounds and the rod 30 of the measuring unit is lowered into the tube 16 until the bottom end of the rod contacts the wet concrete. At this point, the decimal point 52 will appear on the display 72. The slump switch 44 may then be pressed to cause the display 72 to display the flow number representing the slump of the concrete being tested. The temperature of the concrete being tested is displayed by pressing the temperature switch 48.

The tester of this preferred embodiment thus provides an easily used single instrument for testing concrete to determine its slump and temperature.

While one particular embodiment of the present invention has been described in the foregoing, it is to be understood that other embodiments are possible within the scope of the invention. For example, the aluminum foil tube used to modify the inductance of the coil could be replaced with any other device that performed the same, or a similar function, for example some other electrically conductive or magnetic component. The invention is therefore to be considered limited solely by the scope of the appended claims.

I claim:

1. A concrete slump tester comprising:
   a measuring unit comprising an elongate rod, an inductance coil mounted on the rod and means for measuring the inductance of the coil;
   a testing unit comprising a tube for receiving the rod therein, the tube having a lower section for insertion into a body of uncured concrete, an upper section, a plurality of openings in the lower section of the tube for allowing uncured concrete surrounding the lower section of the tube to enter the lower section of the tube at a rate depending on the slump of the concrete, and an inductance modifying tubular metallic element extending along the upper section of the tube for modifying the inductance of the coil as a function of the depth of penetration of the rod into the tube.

2. A tester according to claim 1 wherein the measuring unit comprises a lower rod section with a bottom end, an upper rod section on which the coil is mounted, and an instrument head on an upper end of the upper rod section.

3. A tester according to claim 2 wherein the instrument head includes display means for displaying a flow number representing the inductance of the inductance coil.

4. A tester according to claim 2 wherein the measuring unit includes electrode means exposed at the bottom end of the rod and electric circuit means connected to the electrode means, the electric circuit means including signal means for generating a signal when the electrodes are bridged by a conductive material.

5. A tester according to claim 2 wherein the measuring unit includes temperature sensing means adjacent the bottom end of the rod and display means on the instrument head for displaying the temperature as measured by the temperature sensing means.

6. A tester according to claim 1 wherein the measuring unit comprises a timer and indicator means for indicating when the timer has counted out a predetermined time interval.

7. A concrete tester comprising:
   a testing unit including;
      a tube with a lower section and an upper section;
      a floater disc between the upper and lower sections of the tube;
      at least one opening in the lower section for allowing uncured concrete to flow into the lower section of the tube; and
      an elongate, electrically-conductive element extending along the upper section;
   a measuring unit having;
      an elongate measuring rod sized to extend down the tube of the testing unit to engage concrete in the lower section of the tube with a bottom end of the rod;

an inductance coil mounted on the measuring rod and extending along an upper section thereof to extend into the upper end of the tube;

temperature sensing means adjacent the bottom end of the measuring rod for sensing the temperature of concrete engaged by the bottom end of the rod;

display means;

circuit means coupling the display means to the inductance coil and to the temperature sensing means and including selector means for selectively causing the display means to display the inductance of the coil and the concrete temperature;

electrode means mounted on the measuring rod at the bottom end thereof for engaging concrete in the lower section of the testing unit tube; and concrete contact signal means for signaling the engagement of the electrode means with fresh concrete.

8. A test according to claim 7 including countdown timer means, timer initiating means for selectively initiating the countdown timer means to count down a predetermined time period, and means for causing the display to display the time remaining on the timer during the countdown.

9. A concrete slump tester comprising:
a testing unit including a tube with a lower section, an upper section and at least one opening in the lower section to admit uncured concrete to enter the tube;

a measuring unit comprising an elongate rod sized to extend into the testing unit and having a bottom end for engaging concrete in the tube, electrode means on the bottom end and circuit means coupled to the electrode means and responsive to contact of the electrode means with fresh concrete for generating a signal, and means for measuring the depth of the rod in the tube.

10. A tester according to claim 9 wherein the circuit means comprise means for applying a voltage to one of the electrodes, and means responsive to the presence of a voltage at the other electrode to generate said signal.

11. A tester according to claim 10 wherein said voltage is an AC voltage.

12. A tester according to claim 10 wherein the signal comprises a light signal.

* * * * *